US006153769A

United States Patent [19]
Rüttimann

[11] Patent Number: 6,153,769
[45] Date of Patent: *Nov. 28, 2000

[54] MANUFACTURE OF POLYENE ALDEHYDES

[75] Inventor: August Rüttimann, Arlesheim, Switzerland

[73] Assignee: Roche Vitamins Inc., Parsippany, N.J.

[*] Notice: This patent is subject to a terminal disclaimer.

[21] Appl. No.: 09/193,935

[22] Filed: Nov. 17, 1998

[30] Foreign Application Priority Data

Nov. 27, 1997 [EP] European Pat. Off. .............. 97120814

[51] Int. Cl.$^7$ ................................................. C07D 317/08
[52] U.S. Cl. ........................ 549/430; 549/221; 549/361; 568/447; 568/449
[58] Field of Search ................................... 568/447, 446, 568/449, 459; 549/369, 429, 430, 221, 453

[56] References Cited

U.S. PATENT DOCUMENTS

| | | | |
|---|---|---|---|
| 2,165,962 | 7/1939 | Mueller-Cunradi et al. | 260/615 |
| 2,573,678 | 11/1951 | Saunders | 260/614 |
| 2,827,481 | 3/1958 | Isler et al. | 260/488 |
| 2,827,482 | 3/1958 | Isler et al. | 260/488 |
| 4,832,059 | 5/1989 | Garrard et al. | 131/276 |
| 5,120,864 | 6/1992 | Charbardes et al. | 549/430 |
| 5,266,708 | 11/1993 | Charbades et al. | 549/369 |
| 5,438,073 | 8/1995 | Saurat et al. | 514/452 |
| 5,763,651 | 6/1998 | Rüttimann | 562/509 |
| 5,929,288 | 7/1999 | Rümann | 568/447 |

FOREIGN PATENT DOCUMENTS

| | | |
|---|---|---|
| 0 268 460 | 5/1988 | European Pat. Off. . |
| 630 578 | 12/1994 | European Pat. Off. . |
| 0 816 334 | 1/1998 | European Pat. Off. . |
| 1031301 | 6/1958 | Germany . |
| 1 541 972 | 3/1979 | United Kingdom . |

OTHER PUBLICATIONS

Chemical Abstracts, vol. 57, No. 13, 24 (1962).
Chemical Abstracts, vol. 52, No. 14, 25 (1958).
CA Database Chemlist, XP–002095179 and Annex to Official Journal of the European Communities, (1990).
Hoaglin et al., J. Am.Chem .Soc. 71, 3468–3472 (1949).
Isler et al., Helv. Chim Acta 39, 249–259 (1956).
Isler et al., Helv. Chim Acta 39, 463–473 (1956).
Isler et al., Helv. Chim Acta 42, 854–864 (1959).
Mukaiyama, Org. Reactions, 28, 203–331 (1982).
Nazarov et al., J. Gen. Chem. USSR 28, 2477–2483 (1958).
Makin, Pure & Appl. Chem., 47, 173–181 (1976).
Makin et al., J. Gen. Chem. USSR 31, 3096–3099 (1961).
Makin et al., J. Gen. Chem. USSR 32, 3113–3114 (1962).
Chemla, et al., Bull. Soc. Chim. Fr. 130, 200–205 (1993).
Isler et al., Adv. Org. Chem. 4, 115, p. 160 (1963).
Mukaiyama et al, Chem. Lett. 319–322 (1975).
Mukaiyama et al., Bull. Soc. Chem. Soc. Japan 50, 1161–1168 (1977).
Fleming et al., Tetr. Lett., 34, 3209–3212 (1979).
Fleming, Chimia 34, Nr. 6, 264–271 (1980).
Brownbridge, Synthesis 85–104 (1983).
Mukaiyama et al., Chem. Lett., 1201–1202 (1975).
Mukaiyama et al., Bull. Soc. Chem. Soc. Japan 51, 2077–2081 (1978).
Krasnaya et al., J. Gen. Chem. USSR 32, 63–68 (1962).
Krasnaya et al., J. Gen. Chem. USSR 30, 3875–3882 (1960).
Fishman et al., Synthesis 137–138 (1981).
Holton et al., J. Am.Chem.Soc. 109, 1597–1600 (1987).
Glatz et al., J. Am.Chem.Soc. 101, 2171–2181 (1979).
Schnizer et al., Synlett, 766–768 (1992).
Thomas, J. Am.Chem.Soc. 91, 3281–3289 (1969).
Nazaro et al., J. Gen. Chem. USSR 29, 3649–3654 (1959).
Nazarov et al., J. Gen. Chem. USSR 29, 3641–3648 (1959
Makin, Russian Chem. Rev. 38, 237–248 (1969).
Farmilo et al., Can. J. Res. B28, 689–700 (1950).
Farmilo et al., Can. J. Res. B25, 118–120 (1947).
Chemical Abstract 54, 22 712D (1960) of German Patent 1 031 301.
Chemical Abstract 55, 13409f (1961) of Mikohailov et al., Izv Akad. Nauk. SSSR, Otd. Khim. Nauk. 1903 (1960).
Mukaiyama, Angew. Chem. 89, 858–866 (1977).
Normant et al., Bull. Soc. Chim. Fr. 1646–1650 (1963).
Flaig, Lieb. Ann. Chemie, 568, 1–33 (1949).
Meier, Chem. Ber. 77, 108–110 (1944).

*Primary Examiner*—Sreeni Padmanabhan
*Attorney, Agent, or Firm*—Mark E. Waddell; Stephen M. Haracz; Bryan Cave LLP

[57] ABSTRACT

A process for the manufacture of polyene aldehydes comprises reacting a polyene O,O-ethylene acetal with a 1-alkoxy-1,3-diene in the presence of a Lewis acid or Brönsted acid, hydrolyzing the resulting condensation product and cleaving off alcohol under basic or acidic conditions from the polyene derivative produced at this stage. The novel polyene O,O-ethylene acetals as well as the likewise novel condensation products in this process form further aspects of the invention. The final products are primarily carotenoids which find corresponding use, e.g. as colorants and pigments for foodstuffs, animal products etc.

39 Claims, No Drawings

MANUFACTURE OF POLYENE ALDEHYDES

FIELD OF THE INVENTION

This invention is concerned with the manufacture of polyene aldehydes.

BACKGROUND OF THE INVENTION

Lewis acid-catalyzed additions of α,β-unsaturated ethers (enol ethers) to acetals have been known for a long time and date back to the work of Müller-Cunradi and Pieroh (see U.S. Pat. No. 2,165,962). Hoaglin and Hirsch [J.A.C.S. 71, 3468 et seq. (1949)] investigated this reaction further and broadened the possible applications, which Isler et al. likewise did in the nineteen fifties with respect to the synthesis of β-carotene, crocetin dialdehyde, lycopene as well as β-apocarotenoids [see Helv. Chim. Acta 39, 249 et seq. and 463 et seq. (1956), ibid. 42, 854 et seq. (1959) as well as U.S. Pat. Nos. 2,827,481 and 2,827,482]. Later, Mukaiyama [Angew. Chem. 89, 858 et seq. (1977) and Org. Reactions 28, 203 et seq. (1982)] extended the reaction by using the readily accessible trimethylsilyl enol ethers.

Reactions of ethenol alkyl ethers with cyclic acetals, e.g. ethylene acetals, are also known; they afford by addition cyclic compounds having two ring oxygen atoms, e.g. 1,4-dioxacycloheptane [see Mikhailov et al., Izv. Akad. Nauk. SSSR, Otd. Khim. Nauk. 1960, 1903 et seq./Chem. Abs. 55, 13409 f (1961) and German Patent 1,031,301/ Chem. Abs. 54, 22712 d (1960)].

The first Lewis acid-catalyzed condensations of 1-alkoxy-1,3-dienes (dienol ethers) with α,β-unsaturated acetals were reported by Nazarov and Krasnaya [J. Gen. Chem. USSR 28, 2477 et seq. (1958)] and by Makin [Pure & Appl. Chem. 47, 173 et seq. (1976), J. Gen. Chem. USSR 31, 3096 et seq. (1961) and 32, 3112 et seq. (1962)]. Here, the coupling of the acetal to the dienol ether takes place as far as can be seen exclusively at its γ-position with the formation of a chain-lengthened α,β-unsaturated acetal, which, however, in competition with the first acetal reacts with further dienol ether with the formation of a further, chain-lengthened α,β-unsaturated acetal etc. [telomer formation; see also Chemla et al., Bull. Soc. Chim. Fr. 130, 200 et seq. (1993)]. For this reason such a condensation has been found not to be workable for synthetic purposes, especially for the synthesis of apocarotenoids [Isler et al., Adv. Org. Chem. 4, 115 et seq. (1963)].

Not only 1-alkoxy-1,3-dienes, but also trimethylsilyloxy-dienes [of the type $CH_2=CH-CH=CH-OSi(CH_3)_3$] can be condensed with α,β-unsaturated acetals in the presence of Lewis acid catalysts, as disclosed by Mukaiyama et al. in Chem. Lett. 1975, 319 et seq. In this coupling too the attack seems to take place exclusively at the terminal (γ-) carbon atom of the diene system in order to form "γ-products" [see Mukaiyama et al., Bull. Chem. Soc. Jap 50, 1161 et seq. (1977) and Japanese Patent Publication (Kokai) 36,645/ 1977/Chem. Abs. 87, 201825 t (1977)]. In contrast to the reaction with 1-alkoxy-1,3-dienes, in which an α,β-unsaturated acetal results, the reaction of trimethylsilyloxy-dienes with acetals affords an aldehyde which does not react further with the diene (no telomer formation). Thereby, zinc bromide and many other Lewis acids are required as catalysts only in small amounts [Fleming (et al.), Tetr. Lett. 1979, 3209 et seq. and Chimia 34, 265 et seq. (1980) as well as Brownbridge, Synth. 1983, 85 et seq]. By using this method Mukaiyama et al. were able to synthesize vitamin A [see Kokai 36, 645/1977, Chem. Lett. 1975, 1201 et seq. and Bull. Chem. Soc. Japan 51, 2077 et seq. (1978)] and workers from Rhône-Poulenc developed new routes to carotenoids and vitamin A (see DOS 2,701,489 and A.E.C. Société de Chimie Organique et Biologique No. 7824350).

The aforementioned Lewis acid-catalyzed condensation of a dienol ether with an α,β-unsaturated acetal based on the works of Nazarov and Krasnaya, Makin as well as Chemla et al. would be a very valuable access to apocarotenals and bis-apocarotenals if the yield of the desired primary product of the type . . . $CH=CH-CH(Oalkyl^1)-CH_2-CH=CH-CH (Oalkyl^1)(Oalkyl^2)$ could be increased and the telomer formation could be suppressed. Thus, the desired polyene aldehyde of the type $CH=CH-CH=CH-CH=CH-CHO$ could be obtained from this primary product by hydrolysis of the acetal group $C(Oalkyl^1)(Oalkyl^2)$ and elimination of $alkyl^1OH$. In addition to the fact that in this reaction the formation of the double bond takes place under catalytic conditions, no phosphorus-, silicon- or sulphur-containing reagents are required.

Less known from the scientific literature is the coupling of an (α,β-unsaturated ethylene acetal with a trimethylsily-loxydiene. Analogously to the "usual" dienol ether condensations with dialkyl acetals, the product results in moderate yields [see again Chem. Lett. 1975, 319 et seq. and Bull. Chem. Soc. Japan 50, 1161 et seq. (1977)] according to the equation:

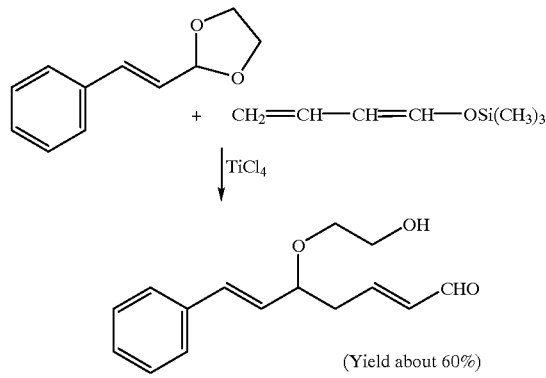

(Yield about 60%)

U.S. Ser. No. 08/865,288 filed May 29, 1997 discloses a different process for the manufacture of polyene aldehydes in which a polyene O,O-dialkyl acetal is reacted with a 1-alkoxy-1,3-diene compound.

An object of the present invention is to manufacture chain-lengthened polyene aldehydes starting from polyene acetals while avoiding as far as possible the aforementioned disadvantages of the state of the art and replacing the Wittig, Horner or Julia reaction hitherto used for this purpose.

SUMMARY OF THE INVENTION

This invention provides a process for the manufacture of polyene aldehydes by reacting a polyene O,O-ethylene acetal with a 1-alkoxy-1,3-diene in the presence of a suitable catalyst, namely a Lewis acid or Brönsted acid, to give the corresponding chain-lengthened δ-alkoxy-α,β-unsaturated polyene aldehyde in the form of its ethylene acetal, hydrolyzing this ethylene acetal to the corresponding aldehyde and finally eliminating the γ-positioned alkanol from this aldehyde under basic or acidic conditions in order to obtain the desired conjugated polyene aldehyde. Not only is the reaction of the 1-alkoxy-1,3-diene with the polyene O,O-ethylene acetal novel, but it takes place (so far as can be seen) with exclusive attack at the γ-position of the alkoxy-diene. The formation of the δ-alkoxy-α,β-unsaturated polyene O,O-ethylene acetal must be seen to be a complete surprise. Through the base- or acid-induced elimination of the alkanol subsequent to the hydrolysis a (conjugated) C-C double bond is formed without requiring a phosphorus-, silicon- or sulphur-containing reagent, which is in contrast to the methodology hitherto usually employed in this field.

DETAILED DESCRIPTION OF THE INVENTION

Accordingly, the present invention provides a process for the manufacture of a polyene aldehyde of the formula

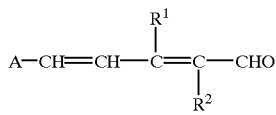

I wherein
- A signifies a monovalent, optionally methyl-substituted, conjugated polyene group and
- $R^1$ and $R^2$ each signify hydrogen or methyl, with the —CH=CH—C($R^1$)=C($R^2$)—CHO group being situated at the terminal position of the conjugated chain of group A, which process comprises reacting a polyene O,O-ethylene acetal of the formula

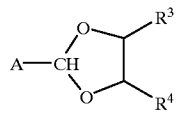

II wherein
- A has the significance given above, with in this case the ethylene acetal group being situated at the terminal position of the conjugated chain of group A, and
- $R^3$ and $R^4$ each signify hydrogen or $C_{1-4}$-alkyl, with a 1-alkoxy-1,3-diene of the formula

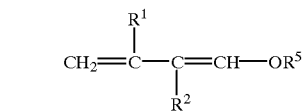

III wherein
- $R^1$ and $R^2$ have the significances given above and
- $R^5$ signifies $C_{1-6}$-alkyl, in the presence of a Lewis acid or Brönsted acid to give the compound of the formula

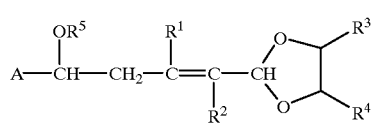

IV wherein A, $R^1$, $R^2$, $R^3$, $R^4$ and $R^5$ have the significances given above,
hydrolyzing the compound of formula IV and cleaving off the alkanol $R^5$OH under basic or acidic conditions from the thus-obtained compound of the formula

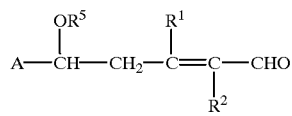

V wherein A, $R^1$, $R^2$ and $R^5$ have the significances given above, with in this case the —CH(OR$^5$)—CH$_2$—C($R^1$)=C($R^2$)—CHO group being situated at the terminal position of the conjugated chain of group A.

The process in accordance with the invention can in principle be used in the case of all of the aforementioned polyene O,O-ethylene acetals of formula II which feature the ethylene acetal group at the end of the polyene chain. Among the suitable educts there are to be found, inter alia, the following sub-classes [with the abbreviated form of presentation which is usual in carotenoid chemistry (using simple lines) being used for the structural formulae]:

Alicyclic-aliphatic polyene O,O-ethylene acetals, which mainly belong to the carotenoid field [as ethylene acetals of asymmetric carotenoid aldehydes having a six-membered (cyclohexene) ring], of the formula

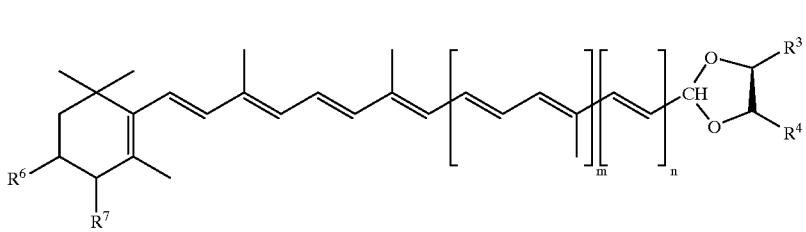

IIa wherein
- $R^3$ and $R^4$ have the significances given above and $R^6$ and $R^7$ each independently signify hydrogen, an optionally protected hydroxy group or an optionally protected oxo group, m signifies 0, 1, 2, 3 or 4 and n signifies 0 or 1, which, after carrying out the multistage process in accordance with the invention, are converted into the corresponding alicyclic-aliphatic polyene aldehydes of the formula

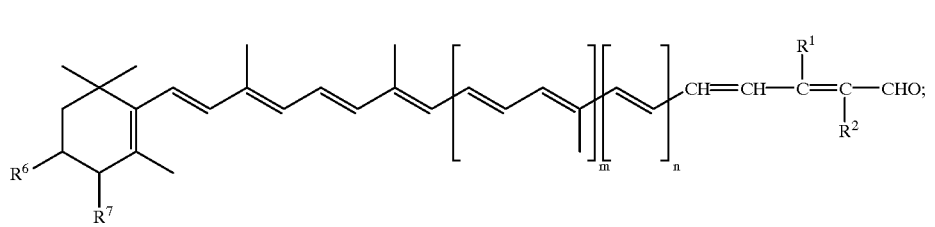

Ia as well as aliphatic polyene O,O-ethylene acetals, which likewise mainly belong to the carotenoid field (as ethylene acetals of open-chain asymmetric carotenoid aldehydes), of the formula

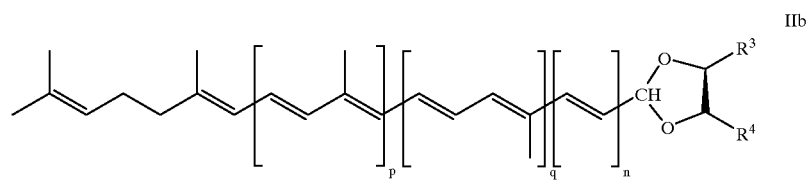

IIb wherein $R^3$ and $R^4$ have the significances given above and p signifies 0,1 or 2, q signifies 0,1 2 or 3 and n signifies 0 or 1, which, after carrying out the multistage process in accordance with the invention, are converted into the corresponding aliphatic polyene aldehydes of the formula

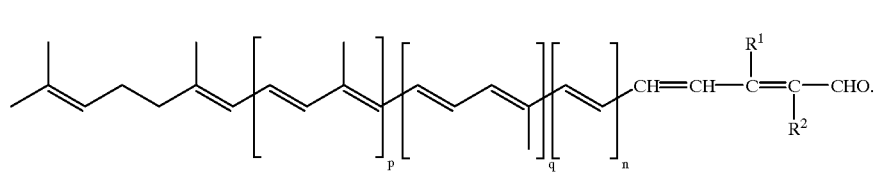

Ib

The educts of formulae IIa and IIb can be embraced by formula II':

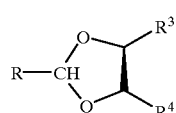

II' wherein

R- signifies a group (a) or (b)

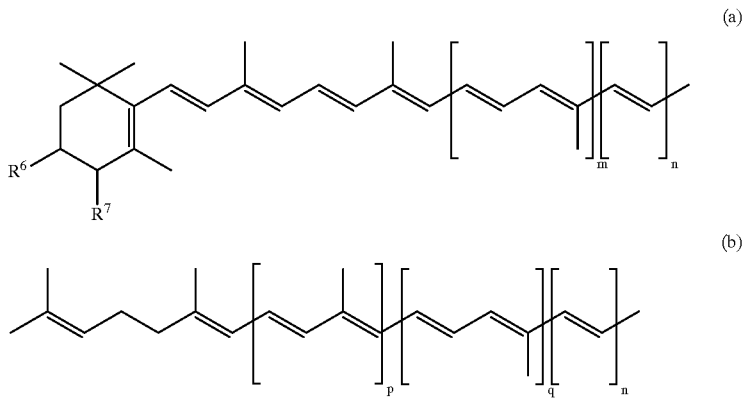

and

R³, R⁴, R⁶, R⁷, m, n, p and q have the significances given above.

After carrying out the multistage process in accordance with the invention the educt of formula II' is converted into the corresponding product of formula I':

$$R-CH=CH-\underset{R^2}{\overset{R^1}{C}}=C-CHO \qquad I'$$

Formula I' then embraces formulae Ia and Ib.

Where the product of formula I, especially of formula Ia, has one or two protected groups (R⁶, R⁷) on the cyclohexene ring, the protecting group(s) present can, if desired, be cleaved off, which represents a further aspect of the present invention.

In the scope of the present invention the term "$C_{1-4}$-alkyl", "$C_{1-5}$-alkyl" or "$C_{1-6}$-alkyl" embraces straight-chain and branched groups such as, for example, methyl, ethyl and isobutyl. This applies analogously to the alkoxy groups.

The term "protected hydroxy group" means a hydroxy group which is protected by a hydroxy protecting group. In accordance with this invention any conventional protected hydroxy group (especially those which are familiar from the carotenoid field) can be utilized, particularly etherified hydroxy groups and acyloxy groups. The "etherified hydroxy groups" are, for example, $C_{1-5}$-alkoxy groups, preferably methoxy and ethoxy; $C_{2-4}$-alkoxyalkoxy groups, preferably 1-methoxy-1-methylethoxy; arylalkoxy groups, preferably benzyloxy; tetrahydropyranyloxy; and tri($C_{1-5}$-alkyl)silyloxy groups, preferably trimethylsilyloxy. The acyloxy groups embrace especially alkanoyloxy and aroyloxy groups with up to 8 carbon atoms such as, for example, formyloxy, acetoxy, propionyloxy and benzoyloxy.

The term "protected oxo group" means an oxo group which is protected by an oxo-protecting group. In accordance with this invention, any conventional protected oxo group can be utilized, especially those which are familiar from the carotenoid field. Acetalized oxo groups, especially those in which the term protected oxo stands for two $C_{1-5}$-alkoxy groups (e.g. two methoxy groups) or for a $C_{2-6}$-alkylenedioxy group (e.g. ethylenedioxy or 2,3-butylenedioxy) are preferred. Further, an oxo group can also be protected as an enol ether, primarily in the case of α-hydroxyketones (e.g. R⁶ and R⁷ signify hydroxy or oxo or vice versa), whereby the esterification of the enediol can preferably also be effected by the formation of a cyclic acetal or ketal (e.g. with acetone to the acetonide). The oxo group can also be protected, for example, as an imine.

The formulae of polyenes disclosed in the scope of the present invention embrace in each case isomeric forms, e.g. optically active and cis/trans or E/Z isomers, as well as mixtures thereof, unless expressly indicated to the contrary. The carbon atom carrying the residue R⁶ or R⁷ where R⁶ or R⁷ signifies an optionally protected hydroxy group (see formulae Ia and IIa) is an example of a chiral (optically active) center. With respect to E/Z isomerism, there are generally preferred the (all-E) isomers of the educts and of the products of the process in accordance with the invention.

The first step of the process in accordance with the invention is conveniently carried out by reacting the polyene O,O-ethylene acetal of formula II with the 1-alkoxy-1,3-diene of formula III in an organic solvent at temperatures in the range of about −60° C. to about +60° C., preferably in the temperature range of about −20° C. to room temperature, and in the presence of a Lewis acid or Brönsted acid. Suitable organic solvents are, in general, all aprotic polar or non-polar solvents. Preferred among such solvents are lower aliphatic and cyclic hydrocarbons, e.g. pentane, hexane and cyclohexane; lower, halogenated aliphatic hydrocarbons, e.g. methylene chloride and chloroform; lower aliphatic and cyclic ethers, e.g. diethyl ether, tert.butyl methyl ether and tetrahydrofuran; lower aliphatic nitriles, e.g. acetonitrile; as well as aromatic hydrocarbons, e.g. toluene. Toluene is the especially preferred solvent. Examples of Lewis acids which can be used are zinc chloride, zinc bromide, titanium tetrachloride, lithium perchlorate, boron trifluoride etherate as well as iron(III) chloride; and of Brönsted acids which can be used are p-toluenesulphonic acid, methanesulphonic acid, trifluoromethanesulphonic acid, sulphuric acid as well as trifluoroacetic acid. These are generally used in catalytic amounts, conveniently in an amount of between about 0.5 and 5 mol percent based on the amount of polyene O,O-ethylene acetal employed and preferably in a mol percent range of 1% to 2%. Moreover, about 1.05 to about 2 equivalents, preferably about 1.2 to about 1.4 equivalents, of 1-alkoxy-1,3-diene are conveniently used per equivalent of polyene O,O-ethylene acetal. Furthermore, the reaction is conveniently effected at normal pressure, although generally the pressure is not critical.

If desired, the intermediate of formula IV can be isolated from the reaction mixture and subsequently hydrolyzed to the corresponding compound of formula V. However, it has been found to be more convenient not to undertake such an isolation and subsequent hydrolysis, but to hydrolyze the intermediate in the reaction mixture itself immediately after completion of the reaction II+III in order in these cases to proceed to the compound of formula V. The hydrolysis can be suitably effected by adding an acid, preferably p-toluenesulphonic acid or slightly diluted aqueous acetic acid, to the reaction mixture and subsequently stifling the mixture for a time, for example about 30 minutes to about 2 hours, conveniently in the temperature range of about 0° C. to room temperature.

The product of formula V can be isolated from the reaction mixture and, if desired, purified in a manner known per se. Typically, the mixture is combined with water and the whole is extracted with a water-immiscible organic solvent such as, for example, with a lower alkane, dialkyl ether or aliphatic ester, e.g. hexane, tert.butyl methyl ether or ethyl acetate, and the organic phase is washed with water and/or sodium bicarbonate solution and/or saturated aqueous sodium chloride, dried and concentrated. The thus-isolated and at least to some extent washed crude product can then, if desired, be purified further, for example by column chromatography, e.g. using eluents such as hexane, ethyl acetate, toluene or mixtures thereof, or (re)crystallization, for example from an alcohol, e.g. methanol or ethanol. Alternatively, and often preferably, the crude product taken up, for example, in a lower alkanol can be reacted directly in the last process step of the present invention, i.e. in the manner of a "through process" II+III→IV→V→I.

With respect to the last process step, i.e. the cleavage of the alkanol $R^5OH$ from the compound of formula V, one can utilize one of the conventional eliminations of the alkanol from β-alkoxyaldehydes or δ-alkoxy- α,β(-unsaturated aldehydes with the formation of the corresponding (α,β-unsaturated aldehydes, which elimination reactions are known from the scientific literature and can be carried out under a variety of conditions. For example, in the manner of known base-induced eliminations 1,8-diaza- bicyclo[5.4.0] undec-7-ene is very often used as the base in an amount of about 2 to 4 equivalents based on the amount of aldehyde used. Such conditions are used in the known production of carotenoids [see, inter alia, Bull. Chem. Soc. Japan 50, 1161 et seq. (1977), ibid. 51, 2077 et seq. (1978), Chem. Lett. 1975, 1201 et seq. and German Offenlegungsschrift 2,701, 489] and of vitamin A (see, inter alia, Chem. Lett. 1975, 1201 et seq.). Aluminium oxide has also been in the production of vitamin A by alkanol cleavage [J. Gen. Chem. USSR 32, 63 et seq. (1962)]. As examples of acid-induced alkanol cleavages reference is again made to Bull. Chem. Soc. Japan 50, 1161 et seq. (1977) and to J. Gen. Chem. USSR 30, 3875 et seq. (1960) in which p-toluenesulphonic acid or 85% phosphoric acid is used as the acid catalyst. The buffer system sodium acetate/acetic acid [Helv. Chem. Acta. 39, 249 et seq. and 463 et seq. (1956) and U.S. Pat. Nos. 2,827,481 and 2,827,482] or sodium formate/formic acid [Synthesis 1981,137 et seq.] has been used for such a cleavage especially in the production of carotenoids.

Furthermore, the cleavage of the alkanol $R^5OH$ can also be carried out using only catalytic amounts of a base, i.e. with less that one equivalent based on one equivalent of the compound of formula V. Thus, the last process step in this case is conveniently carried out by converting the compound of formula V dissolved in a suitable organic solvent into the corresponding polyene aldehyde of formula I in the presence of a catalytic amount of base with cleavage of the alkanol $R^5OH$. Suitable organic solvents are in general protic, aprotic or mixtures thereof such as, for example, alcohols and alcohol mixtures; or aromatic hydrocarbons, e.g. toluene; and lower aliphatic esters, e.g. ethyl acetate. The base can be inorganic or organic, and there are suitable in general strong bases such as, for example, alkali metal alcoholates, e.g. sodium methylate, sodium ethylate, potassium methylate, potassium ethylate and potassium tert.butylate; amines, e.g. triethylamine, 1,5 diazabicyclo[4.3.0]non-5-ene and 1,8-diazabicyclo[5.4.0]undec-7-ene; as well as alkali metal hydroxides and carbonates, especially sodium and potassium hydroxide or carbonate. As mentioned above, a maximum of one equivalent of base per equivalent of the compound of formula V is conveniently used, preferably about 0.05 to about 0.3 equivalent. The reaction is suitably effected in the temperature range of about −20° C. to about 100° C., preferably at temperatures of about 0° C. to about 50° C. Moreover, the reaction is conveniently effected at normal pressure, although in general the pressure is not critical.

It has been found to be especially advantageous to carry out the last process step using a sodium alkoxide as the base and the corresponding alkanol as the solvent at temperatures between about −20° C. and the reflux temperature of the respective reaction mixture, preferably in a temperature range of about 0° C. to about 40° C. Conveniently, either a solution of the sodium alkoxide in the alcohol is prepared in advance or this solution is prepared freshly from metallic sodium and the alkanol. The bringing together of the alkanolic solution of the sodium alkoxide with the solution of the compound of formula V in the (same) alkanol, preferably likewise previously prepared, can be effected in any sequence and preferably at room temperature. The reaction mixture is subsequently stirred and the reaction has normally finished at the latest after one to three hours.

Irrespective of the chosen procedure for the last process step, the product can be isolated from the reaction mixture and purified in a manner known per se. When a basic catalyst is used, the respective working up normally comprises neutralization of the residual base by addition of an organic or inorganic acid such as, for example, a carboxylic acid, e.g. acetic acid, or an aqueous mineral acid, e.g. dilute sulphuric acid.

In the particular embodiment of the procedure described above using a sodium alkoxide as the base, after completion of the reaction the mixture is conveniently cooled to room temperature or even to about 0° C. and thereafter neutralized, preferably with aqueous acetic acid. The crystallization of the product of formula I can also be promoted by further cooling. After its isolation, suitably by filtration, the product can be washed, for example with water and/or aqueous alcohol, and finally dried, optionally under reduced pressure. If desired, further methods such as column chromatography and recrystallization can be employed in order to provide an even purer product.

If desired, protecting groups ($R^6$ and/or $R^7$ as a protected hydroxy or oxo group) which may be present in the obtained product of formula I can be cleaved off according to methods known per se, e.g. by hydrolysis with acid or base.

In the above-defined process in accordance with the invention A or R preferably signifies a group (a) in which $R^6$ and $R^7$ both signify hydrogen and n signifies 0, $R^1$ and $R^2$ preferably signify hydrogen and methyl, respectively, and $R^3$ and $R^4$ both preferably signify hydrogen.

As mentioned above, in carrying out the process in accordance with the invention there is the advantage over the state of the art (especially the aforementioned works of Nazarov and Krasnaya, Makin as well as Chemla et al.) in that, inter alia, the telomer formation is largely suppressed. Although in the process in accordance with the invention the telomer formation resulting from the further reaction of the compound of formula IV with the 1-alkoxy-1,3-diene of formula III cannot always be suppressed completely, this is finally much less serious than expected. The cleavage of the alcohol $R^5OH$ from the compound of V, occurring after the intermediate stage hydrolysis, can be effected readily in the presence of a telomer co-produced in a relatively small amount as a byproduct, e.g. of the formula A—CH($OR^5$)—$CH_2$—C($R^1$)=C($R^2$)—CH($OR^5$)—$CH_2$—C($R^1$)=C($R^2$)—CHO (a single additional reaction), with an analogous alcohol cleavage from the telomer also taking place under the special reaction conditions which are used. However, the latter cleavage does not take place completely in that practically only the alkoxy group $OR^5$ ($\delta$-alkoxy) situated next to the terminal aldehyde group is cleaved off. The result of this incomplete alcohol cleavage from the telomer is that the desired product of formula I can be removed much more readily from the byproduct present at this stage than if all alkoxy groups $OR^5$ had been cleaved off from the telomer. Thus, the byproduct, which still has one or more substituents $OR^5$, remains in the mother liquor of the reaction mixture, while the desired product crystallizes out and is accordingly simple to remove, e.g. by filtration. It is wholly surprising that the telomer loses only the (respective) $\gamma$-positioned alcohol $R^5OH$ in the cleavage step of the process in accordance with the invention.

While some of the educts of the process in accordance with the invention are known, other precursors, which are in part known, can be produced according to methods known per se.

Thus, for example, the novel polyene O,O-ethylene acetals of formula II can be produced very simply in a known general manner by reacting the polyene aldehyde of the formula A—CHO with an optionally alkyl- or dialkyl-substituted 2-lower alkoxy-1,3-dioxolane of the general formula

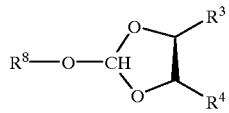

VI wherein $R^3$ and $R^4$ have the significances given above and $R^8$ signifies lower alkyl, preferably $C_{1-4}$-alkyl, especially methyl, in the presence of a catalytic amount of a Lewis acid, e.g. p-toluenesulphonic acid or zinc chloride. The reaction conveniently takes place in an organic solvent, which is suitably an aprotic polar or non-polar solvent. Preferred among such solvents are lower aliphatic hydrocarbons, e.g. hexane; lower halogenated aliphatic hydrocarbons, e.g. methylene chloride and chloroform; lower aliphatic ethers, e.g. diethyl ether; lower aliphatic esters, e.g. ethyl acetate; as well as aromatic hydrocarbons, e.g. benzene and toluene. The reaction is conveniently carried out in the temperature range of about $-20°$ C. to about $+50°$ C., and as a rule takes about 1 to 4 hours. Many examples of the general methodology are known from the literature; see, inter alia, J.A.C.S. 109, 1597 et seq. (1987), ibid. 101, 2171 et seq. (1979) and Synlett 1992, 766 et seq.

The optionally alkyl- or dialkyl-substituted 2-lower alkoxy-1,3-dioxolanes themselves can be produced previously in situ from the corresponding lower alkyl orthoformate and the corresponding optionally alkyl- or dialkyl-substituted ethylene glycol in the presence of an aforementioned Lewis acid. The alkanol $R^8OH$ which thereby results must be removed very carefully, preferably continuously, from the equilibrium, conveniently by continuous evaporation under reduced pressure.

As used herein the term "lower" as in lower aliphatic, lower alkyl, lower alkoxy, lower alkanol etc., means a linear or branched group having from 1 to 6 carbon atoms.

The polyene aldehydes A—CHO in turn are either known, especially from the scientific literature concerning carotenoids, or—where novel—can be produced according to methods known per se. Thus, for example, the reaction of various $C_{15}$-Wittig salts with 2,7-dimethyl-2,4,6-octatriene-1,8-dial (the so-called "$C_{10}$-dial") to give the corresponding monoaldehydes, the reaction of various $C_5$-Wittig aldehydes with long-chain polyene aldehydes likewise to give such monoaldehydes as well as the two-fold reaction of the $C_{10}$-dialdehyde with $C_5$- or $C_{10}$-Wittig aldehydes to give various dialdehydes are known from this literature. The textbooks "Carotenoids" (O. Isler, published by Birkhäuser, Basel and Stuttgart, 1971), especially chapters VI and XII thereof and the further literature mentioned therein, and "Carotenoids, Volume 2 Synthesis" (G. Britton, S. Liaaen-Jensen and H. Pfander, published by Birkhäuser, Basel Boston Berlin, 1996), especially chapters III and VII therein, provide much useful information relating to the production and the occurrence of the known mono- and dialdehydes. Where educts which feature protected hydroxy, oxo or formyl groups are used, such "protected" educts can be produced, for example, directly from the corresponding unprotected educts according to methods known per se.

The 1-alkoxy-1,3-dienes of formula III are in part known compounds; the remaining (novel) compounds can be produced from known starting materials according to methods known per se.

Thus, for example, 1-ethoxy-2-methyl-1,3-butadiene (formula III in which $R^1$ signifies hydrogen, $R^2$ signifies methyl and $R^5$ signifies ethyl) has been known from the literature for a long time [see, inter alia, J.A.C.S. 91, 3281 et seq. (1969), Bull. Soc. Chim. Fr. 1963, 1646 et seq. as well as J. Gen. Chem. USSR 29, 3649 et seq. (1959)] and has in each case been produced by the two-fold cleavage of ethanol from 1,1,3-triethoxy-2-methyl-butane. The butane, in turn, can be produced by an enol ether condensation which has been known for a long time (see U.S. Pat. No. 2,165,962) from the two readily accessible starting materials acetaldehyde diethyl acetal and ethyl (1-propenyl) ether [see in addition J.A.C.S. 71, 3468 et seq. (1949) as well as J. Gen. Chem. USSR 29, 3641 et seq. (1959)]. In this method about 2 to 3 equivalents of the acetal per equivalent of ethyl propenyl ether are heated slightly at about $35°$ C. for up to about 2 hours with about 0.2 mol percent of boron trifluoride etherate as the catalyst in the absence of a solvent, the desired butane being obtained in an about 66% yield. The subsequent two-fold cleavage of ethanol from the 1,1,3-triethoxy-2-methyl-butane has been realized in accordance with the relevant state of the art in two different ways, namely by cleavage in the liquid phase (Bull. Soc. Chim. Fr. 1963, 1646 et seq.) or by cleavage in the gas phase [J. Gen. Chem. USSR 29, 3649 et seq. (1959) and U.S. Pat. No. 2,573,678], preferably according to the latter method.

The 1-methoxy-2-methyl-1,3-butadiene (formula III in which $R^1$ signifies hydrogen and $R^2$ and $R^5$ both signify methyl) is also known from the literature [Japanese Patent Publication (Kokai) 50891/1989]. It can be produced, for example, analogously to the production of 1-ethoxy-2-methyl-1,3-butadiene described above starting from acetaldehyde dimethyl acetal and methyl (1-propenyl) ether via 1,1,3-trimethoxy-2-methyl-butane.

Review articles for the production of 1-alkoxy-1,3-dienes will be found in Russian Chem. Rev. 38, 237 et seq. (1969) and in Pure and Appl. Chem. 47, 173 et seq. (1976); for additional literature concerning their production by gas phase catalysis reference is made to Lieb. Ann. Chem. 568, 1 et seq. (1950), Can. J. Res. B 28, 689 et seq. (1950), ibid. B 25, 118 et seq. (1947) as well as Chem. Ber. 77, 108 et seq. (1944).

The novel starting materials and intermediates of the process in accordance with the invention, i.e. the compounds of formulae II and IV, especially II' and IV' (IV in which the symbol A is replaced by R) represent a further aspect of the present invention.

Among these novel compounds there are to be found:

12'-Apo-β-carotenal ethylene acetal and

8'-Apo-β-carotenal ethylene acetal and, respectively,

12'-methoxy-11',12'-dihydro-8'-apo-β-carotenal ethylene acetal, as well as other such compounds described in the Examples.

The final products of the process in accordance with the invention, i.e. the polyene aldehydes of general formula I, belong for the most part to the carotenoid field. Compounds of formula I can be used as colorants or pigments for foodstuffs, egg yolk, the integuments (especially skin, legs and beak) and/or the subcutaneous fat of poultry, the flesh and/or the integuments (especially skin, scales and shell) of fish and crustaceans etc. This use can be effected according to known methods as described, for example, in European Patent Publication No. 630,578.

European Patent Application no. 97120814.5, filed Nov. 27, 1997 is incorporated herein by reference.

The invention is illustrated on the basis of the following non-limiting Examples.

A. Production of the polyene O,O-ethylene acetals (compounds of the formula II)

EXAMPLE 1

12'-Apo-β-carotenal ethylene acetal 18.6 g (16.7 ml, 0.3 mol) of ethylene glycol, 21.2 g (22 ml, 0.2 mol) of trimethyl orthoformate and 0.1 g of p-toluenesulphonic acid monohydrate were placed in a round flask. The methanol resulting from trans-acetalization was removed on a rotary evaporator at 30°C./100 mbar (10 kPa) for 1 1/2-2 hours to a constant weight of 25 g.

The resulting water-clear solution was then added to a suspension of 35.1 g (0.1 mol) of 12'-apo-β-carotenal in 350 ml of hexane. The reaction mixture was stirred at room temperature, with the educt slowly passing into solution. The product began to crystallize out after about one hour. After a total of 3½ hours 0.5 ml of triethylamine was added thereto, the mixture was poured into 100 ml of water and extracted with 600 ml of diethyl ether, and the solution was washed with 100 ml of saturated sodium chloride solution. After drying with anhydrous magnesium sulphate it was filtered and concentrated. This gave 39.5 g of crude product as yellow needles which were dissolved in 600 ml of diethyl ether, treated with 350 ml of methanol and again freed from ether on a rotary evaporator at 200 mbar (20 kPa). The ice-cold suspension which thereby resulted was suction filtered and the crystals were washed with 300 ml of ice-cold methanol. Drying for eighteen hours at room temperature/ 0.1 mbar (10 Pa) gave 32.7 g (83%) of 12'-apo-β-carotenal ethylene acetal as pale yellow needles with m.p. 128° C.; content according to HPLC: 99.3%; UV (hexane): 392 nm (log ε=4.93), 376 nm (log ε=4.94); IR (no CHO). MS: 394 ($M^+$, 100); $^1$H-NMR (400 MHz, $CDCl_3$): 3.9–4.1 (2m, in each case 2H, $OCH_2CH_2O$), 5.19 (s, 1H,OCHO), no CHO.

Microanalyis:

Calc.: C82.18% H9.71%

Found.: C82.38% H9.78%

EXAMPLE 2

8'-Apo-β-carotenal ethylene acetal 3.7 g (60 mmol) of ethylene glycol, 4.25 g (40 mmol) of trimethyl orthoformate and 20 mg of p-toluenesulphonic acid monohydrate were placed in a round flask. The methanol resulting by trans-acetalization was removed on a rotary evaporator at 30° C./100 mbar (10 kPa) for 2½ hours to a constant weight of 4.4 g.

The resulting solution was then added to 4.17 g (10 mmol) of 8'-apo-β-carotenal in 50 ml of toluene. The reaction mixture was stirred at room temperature for 6 hours. Then it was neutralized with 0.5 ml of triethylamine, diluted with 100 ml of diethyl ether, washed with 50 ml of water and with 50 ml of saturated sodium chloride solution, dried over anhydrous magnesium sulphate, filtered and concentrated on a rotary evaporator. This gave 5.0 g of dark red, oily crystals, which were recrystallized from 20 ml of ethyl acetate (40° C.) and 50 ml of methanol (about 16 hours at 0° C.).

In this manner there were obtained 2.81 g (61%) of 8'-apo-β-carotenal ethylene acetal as reddish crystals with m.p. 135° C. An analytical sample had m.p. 136° C.; content according to HPLC: 99%; UV (cyclohexane/3% $CHCl_3$): 454 nm (log ε=5.04), 443 nm (log ε=5.08); MS: 460 ($M^+$,100); IR (no CHO); $^1$H-NMR (400 MHz, $CDCl_3$): 3.9–4.1 (2m, in each case 2H, $OCH_2CH_2O$), 5.19 (s, 1H, OCHO);

Microanalysis:

Calc.: C83.43% H9.63%

Found.: C83.14% H9.45%

B. Production of the compounds of formulae IV and V

EXAMPLE 3

12'-Methoxy-11',12'-dihydro-8'-apo-β-carotenal ethylene acetal 1.97 g (5 mmol) of 12'-apo-β-carotenal ethylene acetal were suspended in 30 ml of hexane and reacted at 0° C. with 1.1 g (11 mmol) of 1-methoxy-2-methyl-1,3-butadiene in the presence of 10 mg of p-toluenesulphonic acid monohydrate. After 2½ hours the mixture was neutralized with 0.1 ml of triethylamine, diluted with 30 ml of hexane, washed with 25 ml of water, 25 ml of saturated sodium bicarbonate solution and 25 ml of saturated sodium chloride solution, and dried over anhydrous magnesium sulphate, and the solution was concentrated on a rotary evaporator. This gave 2.8 g of a viscous, dark red oil, which was chromatographed on 140 g of silica gel (0.04–0.063 mm) with toluene/hexane (95/5).

In this manner there was obtained 0.49 g (20%) of 12'-methoxy-11',12'-dihydro-8'-apo-β-carotenal ethylene acetal as a (9'E/Z) isomer mixture; $^1$H-NMR (400 MHz, $CDCl_3$): 3.9–4.0 (2 m, in each case 2H, $OCH_2CH_2O$), 5.1 (s, 1H, OCHO), no CHO; MS 492 ($M^+$,100).

EXAMPLE 4

12'-Methoxy-11',12'-dihydro-8'-apo-β-carotenal (through process from 12'-apo-β-carotenal ethylene acetal and 1-methoxy-2-methyl-1,3-butadiene via 12'-methoxy-11',12'-dihydro-8'-apo-β-carotenal ethylene acetal)

1.97 g (5 mmol) of 12'-apo-β-carotenal ethylene acetal were reacted with 0.79 g (8 mmol) of 1-methoxy-2-methyl-1,3-butadiene in 30 ml of toluene in the presence of 19 mg (2 mol %) of p-toluenesulphonic acid monohydrate at −20° C. After 6½ hours at −20° C. 10 ml of 90% aqueous acetic acid were added thereto for the hydrolysis and the mixture was stirred at room temperature for about 30 minutes. Then the mixture was washed twice with 20 ml of water, twice with 20 ml of saturated sodium bicarbonate solution and twice with 20 ml of saturated sodium chloride solution, dried over anhydrous magnesium sulphate and concentrated on a rotary evaporator. This gave 2.7 g of crude 12'methoxy-11', 12'-dihydro-8'-apo-β-carotenal as an orange oil. Chromatography on 135 g of silica gel (0.04–0.063 mm) with toluene/ ethyl acetate (19:1) gave 1.2 g (54%) of 12'-methoxy-11', 12'-dihydro-8'-apo-β-carotenal as an orange, viscous oil. Purity according to HPLC: 95%; IR (film): 1690 cm$^{-1}$ (CHO); MS: 448 (M$^+$, 100); $^1$H-NMR (400 MHz, CDCl$_3$): 3.2 (s, 3H, OCH$_3$), 3.67 (t, 1H, CH—O), 9.40 (s, 1H, CHO).

EXAMPLE 5

8'-Methoxy-7',8'-dihydro-4'-apo-β-carotenal (through process from 8'-apo-β-carotenal ethylene acetal and 1-methoxy-2-methyl-1,3-butadiene via 8'-methoxy-7',8'-dihydro4'-apo-β-carotenal ethylene acetal)

3.35 g (7.5 mmol) of 8β-apo-β-carotenal ethylene acetal were reacted in a 100 ml round flask provided with a magnetic stirrer and argon gasification with 1.3 g (13.5 mmol) of 1-methoxy -2-methyl-1,3-butadiene in 50 ml of toluene in the presence of 30 mg of p-toluenesulphonic acid monohydrate at −10° C. After 3 hours at −10° C. 15 ml of 90% aqueous acetic acid were added in order to hydrolyze the 8'-methoxy-7',8'-dihydro-4'-apo-β-carotenal ethylene acetal formed as the intermediate. The mixture was stirred at room temperature for 2 hours and worked up and chromatographed as described in Example 4. This gave 2.4 g of crude 8'-methoxy-7',8'-dihydro-4'-apo-β-carotenal, which was digested in 30 ml of methanol at 45° C., cooled to 0° C., filtered off and dried.

In this manner there were obtained 1.45 g (36%) of 8'-methoxy-7',8'-dihydro-4'-apo-β-carotenal as an orange solid with m.p. 152–3° C.; purity according to HPLC: 97%; UV (cyclohexane/2% CHCl$_3$): 457 nm (log $\epsilon$=5.03), 430 nm (log $\epsilon$=5.08); $^1$H-NMR (400 MHZ, CDCl$_3$): 3.15 (s, 3H, OCH$_3$); 9.35 (s, 1H, CHO); MS: 514 (M$^+$, 100).

C. Manufacture of the polyene aldehydes of formula I from the compounds of formula V or II and III (through process)

EXAMPLE 6

8'-Apo-β-carotenal 1.16 g (2.6 mmol) of 12'-methoxy-11',12'-dihydro-8'-apo-β-carotenal were dissolved in 15 ml of ethanol in a 50 ml round flask and the solution was treated at room temperature with 0.1 ml (0.5 mmol) of 5.4M sodium methylate solution in methanol, the solution immediately becoming dark and the product crystallizing out slowly. After 30 minutes the mixture was neutralized with 0.2 ml of acetic acid and 1.5 ml of water were added. Then the mixture was cooled, suction filtered and washed once with 2 ml of ethanol/water (19:1) at 0° C., once with 2 ml of water and once with 2 ml of ethanol/water (19:1) at 0° C. The filter material was dried for 3 hours at 50° C.,/1.0 mbar (10 Pa).

In this manner there was obtained 0.80 g (74%) of 8'-apo-β-carotenal as blue-violet crystals with m.p. 135.5–136.5° C.; content according to HPLC: 97.7%.

EXAMPLE 7

8'-Apo-β-carotenal (through process from 12'-apo-β-carotenal ethylene acetal and 1-methoxy-2-methyl-1,3-butadiene via 12'-methoxy-11',12'-dihydro-8'-apo-β-carotenal ethylene acetal and 12'-methoxy-11',12'-dihydro-8'-apo-β-carotenal)

57 mg (2 mol %) of p-toluenesulphonic acid monohydrate were added at −20° C. to a solution of 5.91 g (15 mmol) of 12'-apo-β-carotenal ethylene acetal and 2.36 g (24 mmol) of 1-methoxy-2-methyl-1,3-butadiene in 90 ml of toluene. After 4½ hours 30 ml of 90% aqueous acetic acid were added for the hydrolysis, the cooling was removed and the mixture was stirred at room temperature for 2 hours. The solution was then washed twice with 60 ml of water each time and twice with 30 ml of saturated sodium bicarbonate solution each time and once with 30 ml of saturated sodium chloride solution, dried over anhydrous magnesium sulphate and concentrated. This gave 6.8 g of crude 12'-methoxy-11', 12'-dihydro-8'-apo-β-carotenal as an orange viscous oil. This oil was then dissolved in 100 ml of ethanol at room temperature and treated under argon with about 0.3 ml (16 mmol, 11 mol %) of a 5.4M sodium methylate solution, the solution immediately becoming dark and the product crystallizing out. After 40 minutes the mixture was cooled to 0° C., neutralized with 0.6 ml of acetic acid and 4 ml of water were added dropwise. Then the mixture was filtered, washed with 10 ml of ethanol/water (19:1) at 0° C., twice with 10 ml of water each time and twice with 10 ml of ethanol/water (19:1) each time at 0° C. After drying for 2 hours at 50° C. and 0.1 mbar (10 Pa) there were obtained 4.02 g (63%) of 8'-apo-β-carotenal as blue-violet crystals with m.p. 129–131° C. Content according to HPLC 97.6%.

For further purification, the above product (4.02 g) was dissolved in 70 ml of acetone under reflux for about 10 minutes. Then 25 ml of water were added dropwise to the solution through the condenser under reflux and while stirring vigorously, which gave rise to a crystallization, and then the mixture was cooled slowly to 0° C. After stirring in an ice bath for about 2 hours the precipitate was filtered off and washed twice with in each case 10 ml, a total of 20 ml, of ethanol/water (9: 1) at 0° C, twice with in each case 25 ml, a total of 50 ml, of water and finally three times with in each case 5 ml, a total of 15 ml, of ethanol/water (9:1) at 0° C. After drying under a high vacuum at room temperature there were obtained 3.40 g (54% yield) of pure 8'-apo-β-carotenal as blue-violet metallic glistening crystals with m.p. 138–138.5° C. and a content according to HPLC of 99.5%.

A further 0.3 g (about 5%) of 8'-apo-β-carotenal with m.p. 132° C. could be obtained from the mother liquor by chromatography on silica gel [toluene/ethyl acetate (19:1)]. In total there were obtained 3.7 g (about 59%) of 8'-apo-β-carotenal.

EXAMPLE 8

4'-Apo-β-carotenal 1.30 g (2.37 mmol) of 8'-methoxy-7',8'-dihydro-4'-apo-β-carotenal in 30 ml of methanol/ethyl acetate (1:1) were placed in a 100 ml round flask, treated with 0.1 ml (0.5 mmol) of a 5.4M sodium methylate solution in methanol and stinted at 50° C. for 2 hours. The dark suspension which formed was then cooled (0° C.), filtered off, washed with methanol/water (9:1) and methanol (0° C.) and dried under a high vacuum. This gave 1.0 g (81%) of 4'-apo-β-carotenal as violet crystals with m.p. 155° C. Content according to HPLC: 96%; UV (cyclohexane/2% $CHCl_3$): 491 nm (log ε=5.11); $^1$H-NMR (400 MHz, $CDCl_3$): 9.45 ppm (CHO). MS: 482 ($M^+$, 100%); IR (Nujol): 1680 $cm^{-1}$.

What is claimed is:

1. A process for producing a compound of the formula

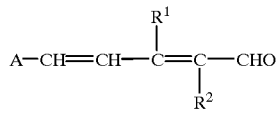

I wherein

A is a monovalent unsubstituted conjugated polyene group or a monovalent methyl-substituted conjugated polyene group and $R^1$ and $R^2$ are each independently hydrogen or methyl, the —CH=CH—C($R^1$)=C($R^2$)—CHO group being situated at the terminal position of the conjugated chain of A, comprising:

a) reacting a polyene O,O-ethylene acetal of the formula

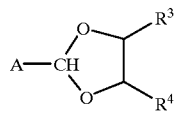

II wherein the ethylene acetal group

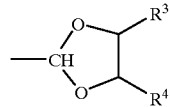

is situated at the terminal position of the conjugated chain of A, and $R^3$ and $R^4$ are each independently hydrogen or $C_{1-4}$-alkyl, with a 1-alkoxy-1,3-diene of the formula

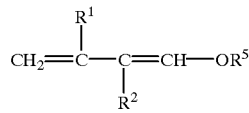

III wherein $R^5$ is $C_{1-6}$-alkyl, in the presence of a catalytic amount of an acid selected from the group consisting of Lewis acids and Brönsted acids to give a compound of the formula

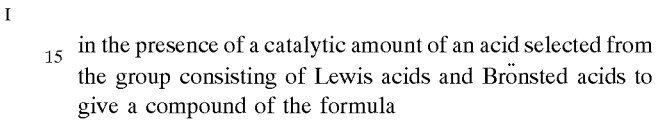

IV b) hydrolyzing the compound of formula IV to give a compound of the formula

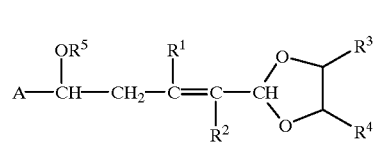

V the —CH($OR^5$)—$CH_2$—C($R^1$)=C($R^2$)—CHO group being situated at the terminal position of the conjugated chain of A; and c) cleaving off the $R^5O$ group under basic or acidic conditions from the compound of formula V, thereby producing the compound of formula I.

2. The process of claim 1, wherein A- is a group of formula

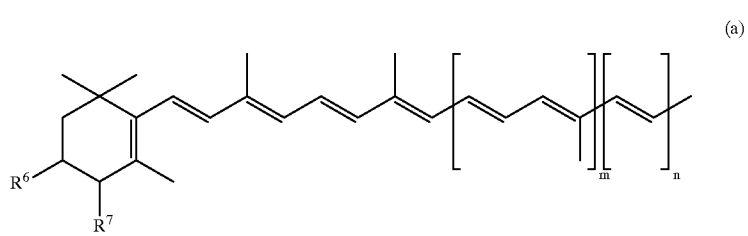

(a)

wherein R⁶ and R⁷ are each independently hydrogen, hydroxy, hydroxy protected by a protecting group, oxo, or oxo protected by a protecting group, m is 0, 1, 2, 3 or 4, and n is 0 or 1.

3. The process of claim 2 wherein at least one of R⁶ and R⁷ is hydroxy protected by a protecting group or oxo protected by a protecting group, further comprising removing from the compound of formula I any protecting group present at R⁶ and R⁷.

4. The process of claim 2, wherein R⁶ and R⁷ are both hydrogen and n is 0.

5. The process of claim 1, wherein A- is a group of formula

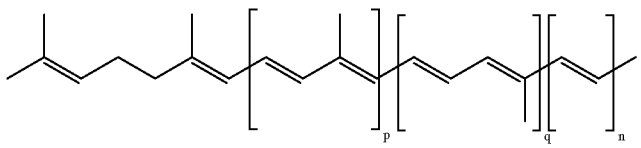

(b)

wherein n is 0 or 1, p is 0, 1 or 2 and q is 0, 1, 2 or 3.

6. The process of claim 1 wherein the acid is a Lewis acid selected from the group consisting of zinc chloride, zinc bromide, titanium tetrachloride, lithium perchlorate, boron trifluoride etherate and iron(III) chloride.

7. The process of claim 1, wherein the acid is a Brönsted acid selected from the group consisting of p-toluenesulphonic acid, methanesulphonic acid, trifluoromethanesulphonic acid, sulphuric acid and trifluoroacetic acid.

8. The process of claim 1, wherein the acid is present in an amount from about 0.5 to about 5 mol percent based on the amount of the polyene O,O-ethylene acetal.

9. The process of claim 1, wherein the ratio of equivalents of the 1-alkoxy-1,3-diene to the polyene O,O-ethylene acetal is from about 1.05:1 to about 2:1.

10. The process of claim 1, wherein the polyene O,O-ethylene acetal is reacted with the 1-alkoxy-1,3-diene in an organic solvent at a temperature in the range of about −60° C. to about +60° C., wherein the organic solvent is a lower aliphatic or cyclic hydrocarbon, a lower halogenated aliphatic hydrocarbon, a lower aliphatic or cyclic ether, a lower aliphatic nitrile or an aromatic hydrocarbon.

11. The process of claim 10, wherein the organic solvent is pentane, hexane, cyclohexane, methylene chloride, chloroform, diethyl ether, tert.butyl methyl ether, tetrahydrofuran, acetonitrile or toluene; and the reaction temperature is from about −20° C. to room temperature.

12. The process of claim 1, wherein the hydrolyzing of the compound of formula IV comprises adding an aqueous solution of a weak acid, and stirring the resulting mixture at a temperature from about 0° C. to room temperature.

13. The process of claim 12, wherein the aqueous solution of a weak acid is dilute acetic acid.

14. The process of claim 1, wherein the cleaving of the R⁵O group comprises reacting the compound of formula V, dissolved in an organic solvent, in the presence of a catalytic amount of a base.

15. The process of claim 14, wherein the base is an alkali alcoholate.

16. The process of claim 15 wherein the alkali alcoholate is sodium methylate, sodium ethylate, potassium methylate, potassium ethylate or potassium tert.butylate.

17. The process of claim 14, wherein the base is an amine.

18. The process of claim 17, wherein the amine is triethylamine, 1,5-diazabicyclo[4.3.0]non-5-ene or 1,8-diazabicyclo[5.4.0]undec-7-ene.

19. The process of claim 14, wherein the base is an alkali metal hydroxide.

20. The process of claim 19, wherein the alkali metal hydroxide is sodium hydroxide or potassium hydroxide.

21. The process of claim 14, wherein the base is an alkali metal carbonate.

22. The process of claim 21, wherein the alkali metal carbonate is sodium carbonate or potassium carbonate.

23. A compound of the formula

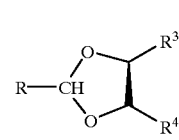

II' wherein

R- is a group of formula

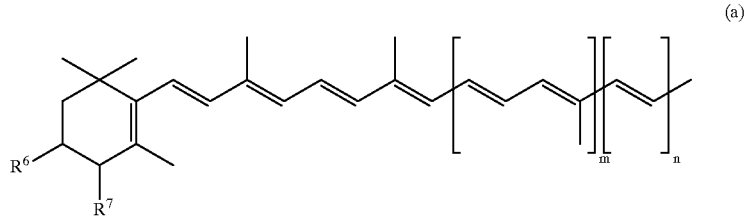

(a)

R³ and R⁴ are each independently hydrogen or $C_{1-4}$-alkyl,

R⁶ and R⁷ are each independently hydrogen, hydroxy, hydroxy protected by a protecting group, oxo, or oxo protected by a protecting group, m is 0, 1, 2, 3 or 4, and n is 0 or 1.

24. The compound of claim 23, wherein m is 1 and n is 0.

25. The compound of claim 24, 12'-apo-β-carotenal ethylene acetal.

26. The compound of claim 23, wherein m is 2 and n is 0.

27. The compound of claim 26, 8'-apo-β-carotenal ethylene acetal.

28. The compound of claim 23, wherein $R^6$ and $R^7$ are hydrogen.

29. The compound of claim 23, wherein $R^3$ and $R^4$ are hydrogen.

30. A compound of the formula

II' wherein

R- is a group of formula (b)

$R^3$ and $R^4$ are each independently hydrogen or $C_{1-4}$-alkyl, n is 0 or 1, p is 0, 1 or 2, and q is 0, 1, 2 or 3.

31. A compound of the formula

IV' wherein

R- is a group of formula $R^1$ and $R^2$ are each independently hydrogen or methyl, $R^3$ and $R^4$ are each independently hydrogen or $C_{1-4}$-alkyl, $R^5$ is $C_{1-6}$-alkyl, $R^6$ and $R^7$ are each independently hydrogen, hydroxy, hydroxy protected by a protecting group, oxo, or oxo protected by a protecting group, m is 1, 2, 3 or 4, and n is 0 or 1.

32. The compound of claim 31, wherein $R^6$ and $R^7$ are hydrogen.

33. The compound of claim 32, wherein n is 0.

34. The compound of claim 33, wherein m is 1.

35. The compound of claim 34, 12'-methoxy-11',12'-dihydro-8'-apo-β-carotenal ethylene acetal.

36. The compound of claim 31, wherein $R^3$ and $R^4$ are hydrogen.

37. The compound of claim 31, wherein $R^1$ is hydrogen and $R^2$ is methyl.

38. The compound of claim 31, wherein $R^5$ is methyl.

39. A compound of the formula

IV' wherein

R- is (a)

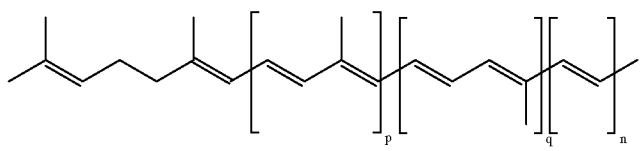
(b)
$R^1$ and $R^2$ are each independently hydrogen or methyl,
$R^3$ and $R^4$ are each independently hydrogen or $C_{1-4}$-alkyl,
$R^5$ is $C_{1-6}$-alkyl,
n is 0 or 1,
p is 0, 1 or 2 and
q is 0, 1, 2, or 3.
* * * * *

UNITED STATES PATENT AND TRADEMARK OFFICE
CERTIFICATE OF CORRECTION

PATENT NO. : 6,153,769
DATED : November 28, 2000
INVENTOR(S) : August Rüttimann

It is certified that error appears in the above-identified patent and that said Letters Patent is hereby corrected as shown below:

Title page,
Under "OTHER PUBLICATIONS," in the third listed Makin et al reference, please change "3113" to -- 3112 --;

Under "OTHER PUBLICATIONS," in the Nazarov et al reference, please change "(1959" to -- (1959) --;

Column 19,
Line 32, please change "perchloratc" to -- perchlorate --;
Line 34, delete "the;"

Column 22,
Line 9, after "m is" insert -- 0 --.

Signed and Sealed this

Fourth Day of December, 2001

Attest:

NICHOLAS P. GODICI
Attesting Officer
Acting Director of the United States Patent and Trademark Office